(12) United States Patent
Bruggeman et al.

(10) Patent No.: US 10,130,781 B2
(45) Date of Patent: *Nov. 20, 2018

(54) COMPRESSIBLE CONNECTOR FOR AN INNER CANNULA

(71) Applicant: COVIDIEN LP, Mansfield, MA (US)

(72) Inventors: Martin Bruggeman, Dublin (IE);
James Michael Ryan, Dublin (IE);
Declan Kiernan, Co. Longford (IE);
Alan Finneran, Co. Ofaly (IE)

(73) Assignee: Covidien LP, Mansfield, MA (US)

( * ) Notice: Subject to any disclaimer, the term of this patent is extended or adjusted under 35 U.S.C. 154(b) by 692 days.

This patent is subject to a terminal disclaimer.

(21) Appl. No.: 14/683,515

(22) Filed: Apr. 10, 2015

(65) Prior Publication Data

US 2015/0209534 A1    Jul. 30, 2015

Related U.S. Application Data (63) Continuation of application No. 13/565,273, filed on Aug. 2, 2012, now Pat. No. 9,010,326.

(51) Int. Cl.
*A61M 16/00* (2006.01)
*A61M 16/04* (2006.01)
*A61M 16/08* (2006.01)

(52) U.S. Cl.
CPC .... *A61M 16/0427* (2014.02); *A61M 16/0429* (2014.02); *A61M 16/0465* (2013.01); *A61M 16/0497* (2013.01); *A61M 16/0434* (2013.01); *A61M 16/0486* (2014.02); *A61M 16/0488* (2013.01); *A61M 16/0816* (2013.01)

(58) Field of Classification Search
CPC .............. A61M 16/04; A61M 16/0488; A61M 16/0463; A61M 16/0427; A61M 16/0434; A61M 16/0497; A61M 16/0816; A61M 16/0465

See application file for complete search history.

(56) References Cited

U.S. PATENT DOCUMENTS

| | | | |
|---|---|---|---|
| 3,169,529 A | 2/1965 | Koenig | |
| 3,225,767 A | 12/1965 | Smith | |
| 3,948,273 A | 4/1976 | Sanders | |
| 4,270,529 A | 6/1981 | Muto | |

(Continued)

FOREIGN PATENT DOCUMENTS

| | | |
|---|---|---|
| CN | 2870876 Y | 2/2007 |
| CN | 201200706 Y | 3/2009 |

(Continued)

OTHER PUBLICATIONS

U.S. Appl. No. 29/428,717—D695,390, Aug. 2, 2012, Dec. 10, 2013, Bruggemann et al.

(Continued)

*Primary Examiner* — Steven Douglas
(74) *Attorney, Agent, or Firm* — Fletcher Yoder PC (57) ABSTRACT

A tracheal tube assembly includes an outer cannula configured to be positioned in a patient airway and an inner cannula configured to be disposed inside the outer cannula. The tracheal tube assembly further includes a flange member secured about the outer cannula, and an outer cannula connector coupled to a proximal end of the outer cannula. The inner cannula includes a compressible proximal end region that is compressed while secured inside the outer cannula connector.

20 Claims, 9 Drawing Sheets

(56) References Cited

U.S. PATENT DOCUMENTS

| | | | |
|---|---|---|---|
| 4,315,505 A | 2/1982 | Crandall et al. |
| 4,817,598 A | 4/1989 | LaBombard |
| 4,909,248 A | 3/1990 | McLennan |
| 5,386,826 A | 2/1995 | Inglis et al. |
| 5,471,980 A | 12/1995 | Varner |
| 5,762,638 A | 6/1998 | Shikani et al. |
| 5,864,938 A | 2/1999 | Gansel et al. |
| 5,996,582 A | 12/1999 | Turnbull |
| 6,019,753 A | 2/2000 | Pagan |
| 6,024,730 A | 2/2000 | Pagan |
| 6,105,577 A | 8/2000 | Varner |
| 6,135,110 A | 10/2000 | Roy |
| 6,248,099 B1 | 6/2001 | Bell |
| 6,588,426 B2 | 7/2003 | Linderoth |
| D479,876 S | 9/2003 | Gradon et al. |
| 6,679,871 B2 | 1/2004 | Hahnen |
| 6,722,367 B1 | 4/2004 | Blom |
| 6,725,862 B2 | 4/2004 | Klinberg et al. |
| 6,739,339 B2 | 5/2004 | Bergamaschi |
| 6,796,309 B2 | 9/2004 | Nash et al. |
| 6,840,242 B1 | 1/2005 | McCoy |
| 7,086,402 B2 | 8/2006 | Peterson |
| 7,156,090 B2 | 1/2007 | Nomori |
| 7,305,989 B2 | 12/2007 | Gostelow |
| 7,341,061 B2 | 3/2008 | Wood |
| D585,980 S | 2/2009 | Cabrera |
| 7,681,576 B2 | 3/2010 | Thomas et al. |
| 7,987,851 B2 | 8/2011 | Blom et al. |
| 8,127,766 B2 | 3/2012 | Chang |
| 2004/0068278 A1 | 4/2004 | Fleischman et al. |
| 2004/0154623 A1 | 8/2004 | Schaeffer et al. |
| 2004/0177851 A1 | 9/2004 | Acosta |
| 2005/0066816 A1 | 3/2005 | Wright |
| 2005/0166924 A1 | 8/2005 | Thomas et al. |
| 2005/0241643 A1 | 11/2005 | Webber |
| 2006/0070628 A1 | 4/2006 | Byatt et al. |
| 2006/0081254 A1 | 4/2006 | Gostelow |
| 2006/0124134 A1 | 6/2006 | Wood |
| 2007/0012317 A1 | 1/2007 | Flagler et al. |
| 2007/0181130 A1 | 8/2007 | Worley |
| 2007/0246051 A1 | 10/2007 | Newman |
| 2007/0255258 A1 | 11/2007 | Matlock et al. |
| 2008/0072911 A1 | 3/2008 | Flagler et al. |
| 2008/0142001 A1 | 6/2008 | Wright |
| 2008/0142003 A1 | 6/2008 | Depel |
| 2008/0149108 A1 | 6/2008 | Neame |
| 2008/0216839 A1 | 9/2008 | Rutter |
| 2008/0257353 A1 | 10/2008 | Yamamoto et al. |
| 2009/0025717 A1 | 1/2009 | Pinel |
| 2009/0145440 A1 | 6/2009 | Bierman et al. |
| 2010/0089403 A1 | 4/2010 | Solly |
| 2010/0108076 A1 | 5/2010 | Chang |
| 2010/0244432 A1 | 9/2010 | Neame et al. |
| 2010/0307488 A1 | 12/2010 | Poulsen et al. |
| 2010/0319705 A1 | 12/2010 | Thomas et al. |
| 2011/0083672 A1 | 4/2011 | Webster et al. |
| 2012/0103341 A1 | 5/2012 | Behlmaier |

FOREIGN PATENT DOCUMENTS

| | | |
|---|---|---|
| CN | 101474448 A | 7/2009 |
| CN | 201437019 U | 4/2010 |
| CN | 101801653 A | 8/2010 |
| CN | 201811084 U | 6/2011 |
| CN | 102256652 A | 11/2011 |
| CN | 202028015 U | 11/2011 |
| EP | 1803478 A1 | 7/2007 |
| WO | WO2008046418 A1 | 4/2008 |
| WO | WO2011149664 A1 | 12/2011 |
| WO | WO2012064479 A1 | 5/2012 |

OTHER PUBLICATIONS

U.S. Appl. No. 29/428,719—D695,889, Aug. 2, 2012, Dec. 17, 2013, Bruggemann et al.
U.S. Appl. No. 13/776,194—US2014-0238389, Feb. 25, 2013, Aug. 28, 2014, Bruggemann et al.
U.S. Appl. No. 13/565,273—US20140034048, Feb. 6, 2014, Bruggemann et al.
Rusch Crystal (2010) http://www.teleflexmedical.com/prod_rusch.php.
Percutan (2010) http://www.tracoe.com/products.html.
Pure (2010) http://www.tracoe.com/products.html.
Twist (2010) http://www.tracoe.com/products.html.
Mini (2010) http://www.tracoe.com/products.html.
Comfort (2010) http://www.tracoe.com/products.html.
Rusch Tracheoflex (2010) http://www.teleflexmedical.com/prod_rusch.php.
Silicone Air Cuff Tracheostomy Tubes, Pediatric & Neonatal TT, Adjustable Neck Flange TT; (2010) http://www.arcadiamedical.com/arcadia/main.asp?cid=4&pid=2.
Silicone Cuffless Adult Tracheostomy Tubes; (2010) http://www.arcadiamedical.com/arcadia/main.asp?cid=4&pid=2.
Bivona Adult Fome-Cuf (2013) http://www.smiths-medical.com/catalog/endotracheal-tubes.
Bivona Aire-Cuf Neonatal and Pediatric (2013) http://www.smiths-medical.com/catalog/endotracheal-tubes.
Portex Blue Line Cuffed (2013) http://www.smiths-medical.com/catalog/endotracheal-tubes.
Portex Blue Line Uncuffed (2013) http://www.smiths-medical.com/catalog/endotracheal-tubes.
Bjorling et al., "Clinical Use and Material Wear of Polymeric Tracheostomy Tubes", Laryngoscope 117: Sep. 2007.
Liu, et al., "Extra-long Montgomery T Tube in Major Airway Stenosis", The Journal of Laryngology & Otology (2008), 123, 772-777.
U.S. Appl. No. 29/428,717 file history, filed Aug. 2, 2012.
U.S. Appl. No. 29/428,719 file history, filed Aug. 2, 2012.
U.S. Appl. No. 13/776,194 file history, filed Feb. 25, 2013.
U.S. Appl. No. 13/565,273 file history, filed Feb. 6, 2014.
Lazarus medical; Securing Critical Connections—Phoneris Inner Cannulae and Phoneris AeroFlex—5011 Rev. 2; 5006 Rev. 3.
204A extra-long speaking tube, type B; http://www.kapitex.com/tracheostomy/tracoecomfort/tracoecomfort-204a/.
sales@bryanmedical.net; TRACOE TWIST ref 304 http://www.bryanmedical.net/Tracoe/Tracoe_Twist304.html.
Portex Tracheostomy Care Handbook.
Portex Uniperc Tube Brochure 2.
International Search Report and Written Opinion for PCT Application No. PCT/US2013/052867 dated Dec. 26, 2013; 7 pgs.
Chinese Office Action dated Mar. 1, 2016 in Application No. 201380041091.7.
Chinese Office Action for CN Application No. 201380041091.7 dated Nov. 3, 2016; 6 Pages.
CN Notice of Allowance & Search Report for CN Application No. 201380041091.7 dated Mar. 10, 2017; 4 Pages.

COMPRESSIBLE CONNECTOR FOR AN INNER CANNULA

CROSS REFERENCE TO RELATED APPLICATIONS

This application is a continuation of prior U.S. application Ser. No. 13/565,273, filed Aug. 2, 2012, the specification of which is incorporated herein by reference in its entirety for all purposes.

BACKGROUND

The present disclosure relates generally to the field of tracheal tubes and, more particularly, to a tracheal tube including an inner cannula with a compressible end.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

A wide variety of situations exist in which artificial ventilation of a patient may be desired. For short-term ventilation or during certain surgical procedures, endotracheal tubes may be inserted through the mouth to provide oxygen and other gasses to a patient. For other applications, particularly when longer-term intubation is anticipated, tracheostomy tubes may be preferred. Tracheostomy tubes are typically inserted through an incision made in the neck of the patient and through the trachea. A resulting stoma is formed between the tracheal rings below the vocal chords. The tracheostomy tube is then inserted through the opening. In general, two procedures are common for insertion of tracheostomy tubes, including a surgical procedure and a percutaneous technique.

Such tubes may include an inner cannula, such as a reusable inner cannula, or a disposable inner cannula. The inner cannula may be disposed inside the tracheostomy tube and used as a conduit for liquids or gas incoming and outgoing into the patient's lungs. The inner cannula may be removed for cleaning and for disposal of secretions without disturbing the placement of the tracheostomy tube. A connector is typically provided at an upper or proximal end where the tube exits the patient airway, suitable for coupling the ventilator with the inner cannula. In one embodiment, the inner cannula may be removed, cleaned, and reused. In another embodiment, the inner cannula may be disposable, and a new inner cannula may then be positioned inside of the tracheal tube. By enabling the cleaning and/or replacement of the inner cannula, a ventilation circuit may be kept clean and free of secretions.

Standard connectors have been developed to allow the tracheal tube to then be fluidly coupled to artificial ventilation equipment to supply the desired air or gas mixture to the patient, and to evacuate gases from the lungs. One difficulty that arises in the use of tracheal tubes, and tracheostomy tubes in particular, is in the connection of the tube to the ventilation equipment. For example, an inner cannula may not be installed, or may be installed improperly. This may lead to difficulties with ventilation when a connection is made to ventilation equipment.

There is a need, therefore, for improved tracheal tubes, and particularly for improved tracheostomy tubes. It would be desirable to provide a tube that allows for ease of placement and connection of the inner cannula during ventilation.

BRIEF DESCRIPTION

This disclosure provides a novel tracheal tube designed to respond to such needs with a low insertion force and a high retention force. The tracheal tube may be a tube with a separate inner cannula and outer cannula. The inner cannula includes a compressible end, such as a pinch end, that allows for ease of insertion into the outer cannula. In contrast to other types of inner cannula connectors, such as threaded or snap-on connectors, the disclosed embodiments may provide inner cannulas that may be inserted and connected in a single movement and that also resist axial or rotational displacement relative to the outer cannula. In particular embodiments, the entire proximal end of the inner cannula, including any cap or lip portion, is smaller in diameter than the widest portion of the outer cannula connector when properly inserted. In this manner, the outer cannula connector forms the connector portion (e.g., a standard 15 mm connector) for attachment to upstream medical tubing and/or devices. This is in contrast to disposable inner cannulas that, when inserted into an outer cannula and connector, have integral 15 mm connectors. Accordingly, in the disclosed embodiments, the standard connector resides on the outer cannula portion of the tracheal tube, which may allow the outer cannula assembly to be connected to upstream medical tubing with or without an inserted inner cannula.

Further, the compressible end of the inner cannula may be adhered to or otherwise affixed to the inner cannula to form its proximal end region or may be manufactured as a unitary assembly, such as a single molded piece, which may be a cost-effective manufacturing technique. The disclosed tracheal tubes provide improved inner/outer cannula connection while also maintaining standard connections to other medical tubing, such as ventilator tubing.

Thus, in accordance with a first aspect, a tracheal tube assembly includes an outer cannula configured to be positioned in a patient airway. The assembly further includes a flange member secured about the outer cannula and an outer cannula connector coupled to a proximal end of the outer cannula. The assembly further includes an inner cannula configured to be disposed inside the outer cannula such that the inner cannula and the outer cannula are coaxial. The inner cannula features a compressible proximal region that is configured to be positioned inside the outer cannula connector. The compressible proximal region is capable of assuming a compressed configuration and an uncompressed configuration. The compressed configuration is assumed when the compressible proximal end region is positioned in the outer cannula connector, and the uncompressed configuration is assumed when the compressible proximal end region is not subjected to any biasing forces.

In accordance with another aspect, a tracheal tube inner cannula includes a conduit configured to be inserted into an outer cannula to transfer gas to a patient, the conduit comprising a flared proximal region, wherein the flared proximal region is configured to be inserted in an outer cannula connector. The flared proximal region includes a first ear and a second ear separated by opposing notches formed in a wall of the flared proximal region, wherein the opposing notches extend from the flared proximal region towards a distal end of the inner cannula such that an outer circumference of a proximal end of the inner cannula is a broken annulus and wherein the first ear and the second ear are configured to be biased towards one another when the flared proximal region is inserted in the outer cannula connector.

Also disclosed herein is a tracheal tube assembly kit that includes an outer cannula configured to be positioned in a patient airway; a flange member secured about the outer cannula; an outer cannula connector coupled to a proximal end of the outer cannula; and an inner cannula configured to be disposed inside the outer cannula comprising: a conduit configured to be inserted into an outer cannula to transfer gas to a patient, the conduit comprising a flared proximal region, wherein the flared proximal region is configured to be inserted in an outer cannula connector and wherein the flared proximal region comprises a first ear and a second ear separated by opposing gaps formed in a wall of the flared proximal region, wherein the first ear and the second ear are configured to be biased towards one another when the flared proximal region is inserted in the outer cannula connector.

Also disclosed herein is a tracheal tube inner cannula mold. The mold includes a mold form defining a conduit, wherein the conduit comprises: a distal end; a flared proximal region comprising a first ear and a second ear separated by opposing notches formed in a wall of the flared proximal region, wherein the opposing notches extend from the flared proximal region towards a distal end of the inner cannula such that an outer circumference of a proximal end of the inner cannula is a broken annulus; a first protrusion formed on an outer surface of the first ear and a second protrusion formed on an outer surface of the second ear, wherein the opposing notches extend distally past the first protrusion and the second protrusion.

BRIEF DESCRIPTION OF THE DRAWINGS

Various aspects of the disclosed techniques may become apparent upon reading the following detailed description and upon reference to the drawings in which.

DETAILED DESCRIPTION OF SPECIFIC EMBODIMENTS

One or more specific embodiments of the present techniques will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

The tracheal tubes as provided herein are disposable rather than reusable, capable of providing differential mechanical ventilation to either or both lungs, and capable of supporting all other functions of standard tracheal tubes (e.g. sealing, positive pressure generation, suctioning, irrigation, drug instillation, etc). The tracheal tubes can be used in conjunction with all acceptable auxiliary airway devices such as (e.g. heat and humidity conservers, mechanical ventilators, humidifiers, closed suction systems, scavengers, capnometers, oxygen analyzers, mass spectrometers, PEEP/CPAP devices, etc). Furthermore, although the embodiments of the present disclosure illustrated and described herein are discussed in the context of tracheal tubes such as tracheostomy tubes, it should be noted that presently contemplated embodiments may include a tracheal tube assembly including an inner cannula with a compressible end used in conjunction with other types of airway devices. For example, the disclosed embodiments may be used in conjunction with a single-lumen tube, an endotracheal tube, a double-lumen tube (e.g., a Broncho-Cath™ tube), a specialty tube, or any other airway device with a main ventilation lumen. Indeed, any device with a ventilation lumen designed for use in an airway of a patient may include an inner cannula with a compressible end as provided. As used herein, the term "tracheal tube" may include an endotracheal tube, a tracheostomy tube, a double-lumen tube, a broncho-blocking tube, a specialty tube, or any other airway device.

Figure 1:
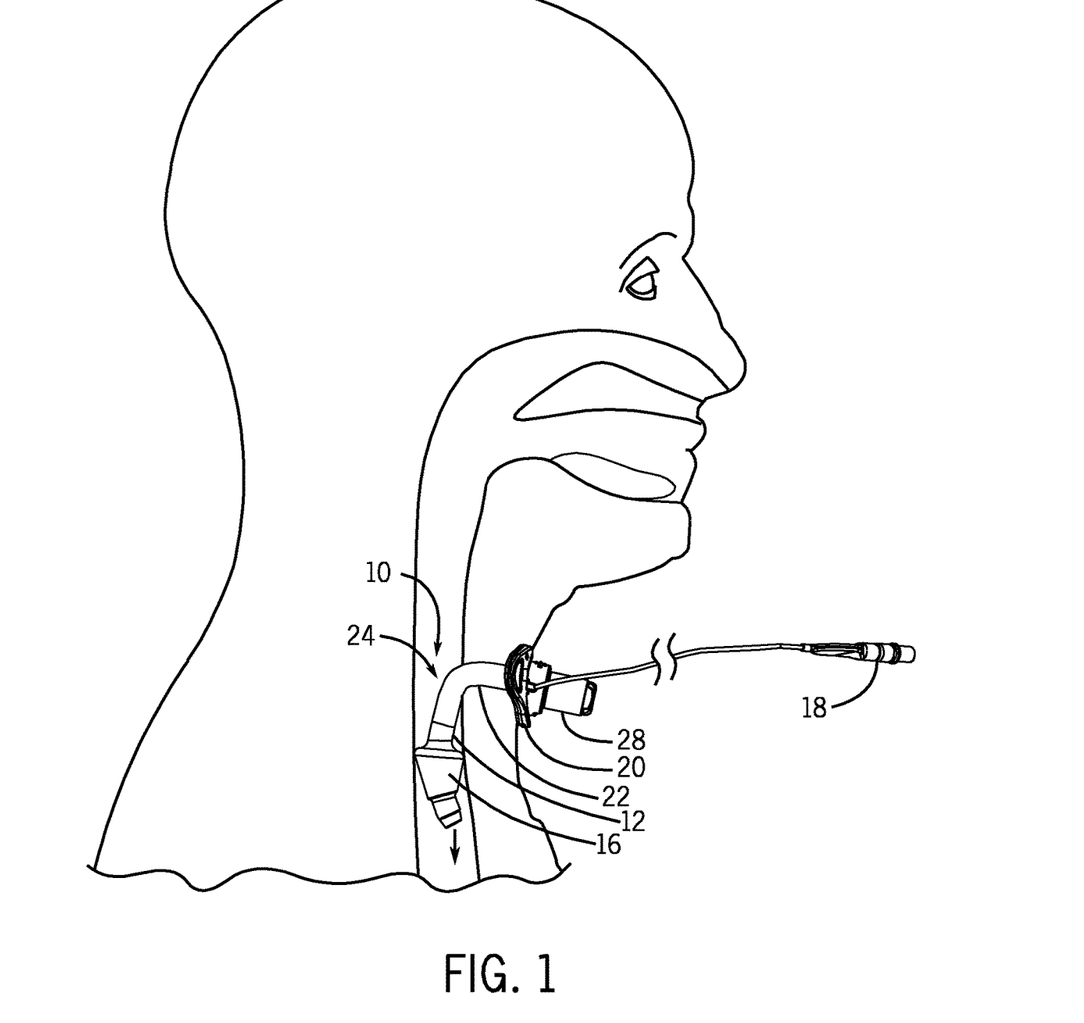
FIG. 1 is a perspective view of a tracheal tube with a compressible inner cannula connector inserted into a patient in accordance with embodiments of the present disclosure.

Turning now to the drawings, FIG. 1 is a perspective view of an exemplary tracheal tube 10 placed in a patient's airway in accordance with aspects of the present disclosure. The tracheal tube assembly 10 represented in the figures is a tracheostomy tube, although aspects of this disclosure could be applied to other tracheal tube structures, such as endotracheal tubes. The application to a tracheostomy tube is apt, however, insomuch as such tubes tend to be worn for longer periods of time and, thus, may include a removable and/or disposable inner cannula disposed inside of an outer cannula 12, which is useful in maintaining a clean ventilation circuit.

The tracheal tube 10 includes an outer cannula 12 that defines a ventilation lumen and that facilitates the transfer of gases to and from the lungs. The tracheal tube 10 includes an inflatable cuff 16 disposed on the outer cannula 12. However, certain embodiments of the disclosure may be used in conjunction with cuffless tubes. A proximal end of the tracheal tube 10 may connect to upstream airway devices (e.g., a ventilator) via the appropriate medical tubing and/or connectors. In embodiments that include a cuff 16, a pilot balloon and inflation line assembly 18 is coupled to the cuff 16.

The outer cannula 12 is illustrated extending both distally as well as proximally from a flange member 20. A pair of side wings of the flange 20 extend laterally and serve to allow a strap or retaining member (not shown) to hold the tube assembly 10 in place on the patient. In one embodiment, apertures formed in each side of the flange member 20 allow the passage of such a retaining device. In many applications, the flange member 20 may be taped or sutured in place as well. During intubation, the tracheal tube assembly 10 is placed through an opening formed in the neck and trachea of a patient and extending into the patient airway. In certain embodiments, the tracheal tube assembly 10 is curved to accommodate the curved tracheal passageway. For example, the outer cannula 12 may be curved in an unbiased state (i.e., outside the patient) such that an inner curve 22 is generally positioned on a ventral side of the patient while the outer curve 24 is positioned on the dorsal side of the patient when the tracheal tube assembly 10 is inserted in the patient. Further, while a distal portion of the outer cannula 12 is inserted within the patient, a proximal portion of the outer cannula 12 forms an outer cannula connector 28. As provided herein, the outer cannula connector 28 receives a compressible end region of the inner cannula and forms a secure connection.

Figure 2:
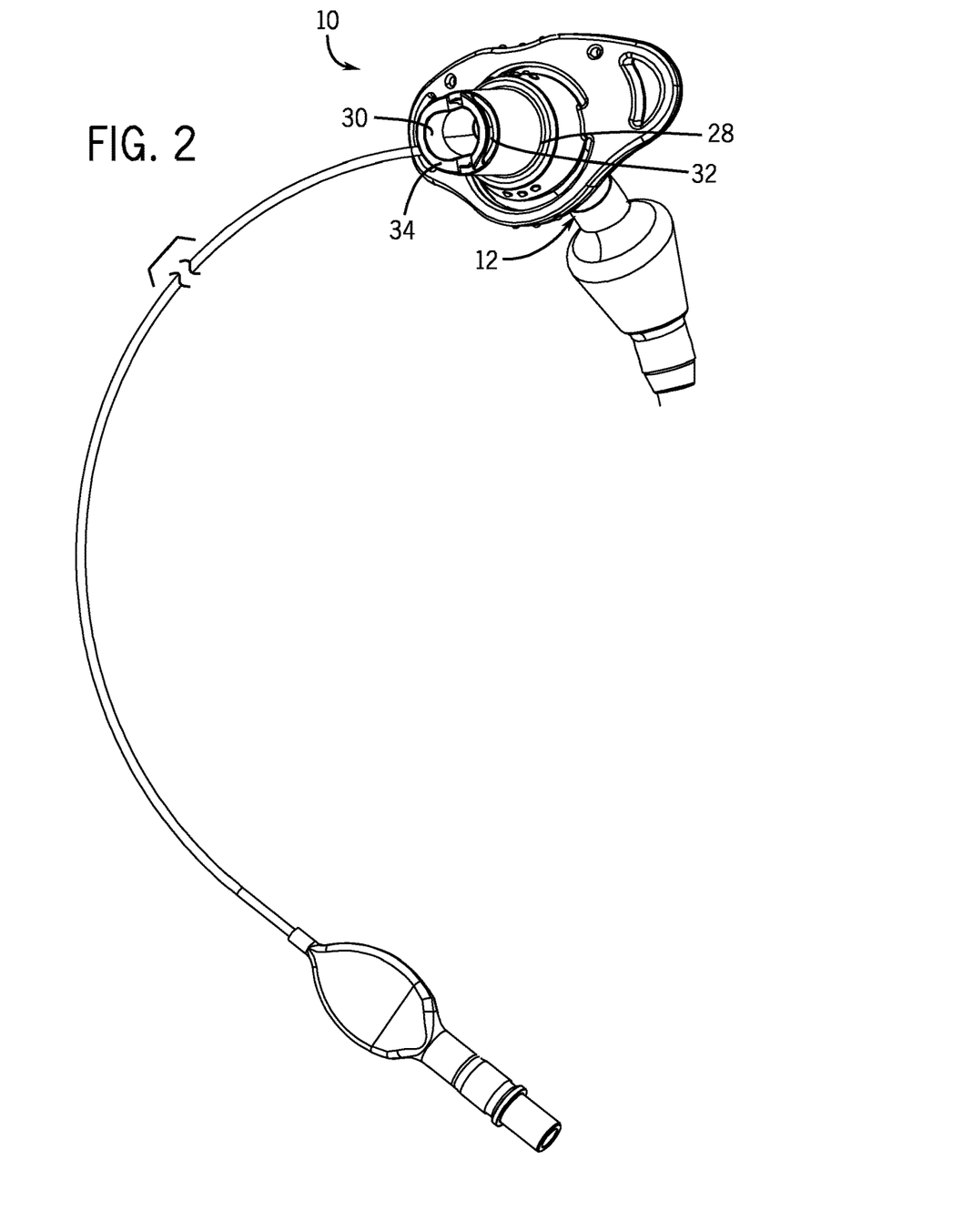
FIG. 2 is a perspective view of the tracheal tube of FIG. 1.

FIG. 2 is a perspective view of the tracheal tube assembly 10 showing an inner cannula 30 inserted in the outer cannula 12 and forming a connection with the outer cannula connector 28. The compressible end region 32 is disposed within the outer cannula connector 28 such that a proximal end 34 is exposed (i.e., is not within the outer cannula connector 28). The inner cannula 30 is generally coaxial with the outer cannula 12 and is shaped to fit within the outer cannula 12 to form the gas conveying passageway to the patient. In this manner, the inner cannula 30 may be removed and replaced while the outer cannula 12 is retained. This reduces stress on the stoma while permitting cleaning of the passageway.

Figure 3:
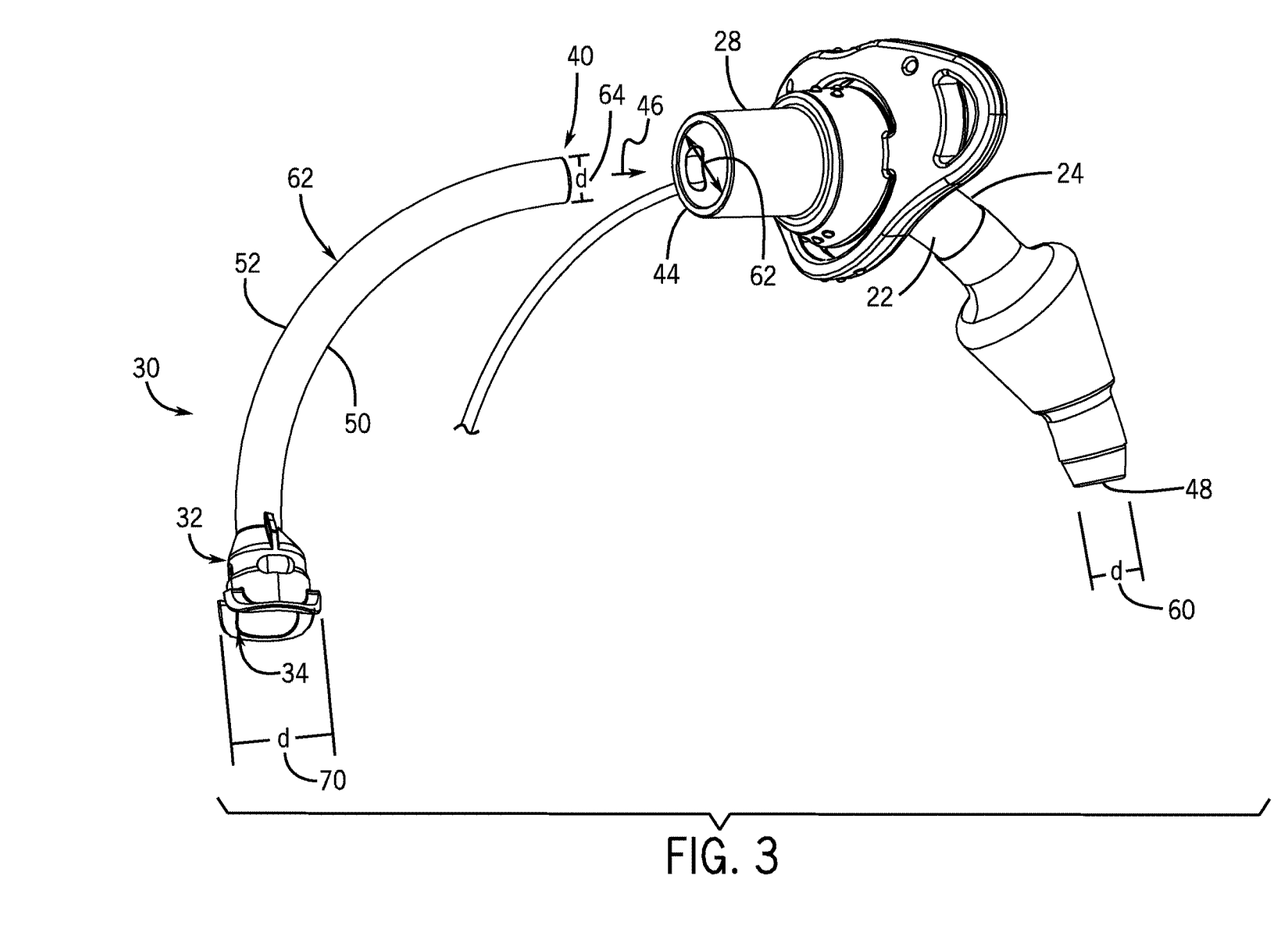
FIG. 3 is a perspective view of a separate inner cannula and outer cannula assembly of the tracheal tube of FIG. 1.

The inner cannula 30 may be manually inserted into the outer cannula 12. As shown in FIG. 3, the inner cannula 30 may be inserted by pushing the distal end 40 through the proximal end 44 of the outer cannula 12, e.g., in the direction of arrow 46. The insertion is complete when the distal end 40 is generally located at or near the distal end 48 of the outer cannula 12. In certain embodiments, the distal end 40 of the inner cannula 30 terminates short of the distal end 48 of the outer cannula and is disposed entirely within the outer cannula. When the inner cannula 30 is inserted, the compressible end region 32 is disposed at least in part within the outer cannula connector 28. In embodiments in which the outer cannula forms a curve, such as a Magill curve, the inner cannula 30 may also be curved in a complementary fashion. Accordingly, the insertion may be directional such that proper insertion involves an inner curve 50 of the inner cannula 30 located proximate to or corresponding with the inner curve 22 of the outer cannula 12. Similarly, the outer curve 52 of the inner cannula 30 will be located proximate to the outer curve 24 of the outer cannula 12. The positioning of the inner cannula 30 in the outer cannula 12 may be facilitated by operator technique and, in particular embodiments, with the aid of markings, instructions, or other visual indicators.

The inner cannula 30 forms a conduit from which liquids or gases, including medications, may enter through the proximal end 34. Both the inner cannula 30 and the outer cannula 12 have dimensions selected to fit easily through the stoma. In practice, a range of such tubes may be provided to accommodate the different contours and sizes of patients and patient airways. Such tube families may include tubes designed for neonatal and pediatric patients as well as for adults. By way of example only, the outer cannula 12 of the tube 10 may range from 4 mm to 16 mm. The inner cannula 30 may be sized to correspond with an appropriate outer cannula 12. The outer cannula 12 and the inner cannula 30 may be characterized by their inner diameters (referring to the diameter of the interior of the passageway) or their outer diameters (referring to the diameter as measured from the exterior outside wall to exterior outside wall).

Because the inner cannula 30 fits within the outer cannula 12, the outer cannula 12 features a larger inner diameter 60 relative to an outer diameter 64 of the inserted portion 54 of the inner cannula 30. The outer diameter 64 of the inner cannula 30 may be selected to allow sufficient air flow while also fitting comfortably within the outer cannula 12 and allowing for appropriate insertion force. The inner diameter of the outer cannula 12 is less than the outer diameter 64 by the thickness of the walls of the inner cannula 30. For example, an inner cannula 30 sized to 6.5 mm may have an outer diameter 64 of about 6.5 mm and an inner diameter of about 5.5 mm. In such an embodiment, the inner cannula walls are about 1 mm thick in the inserted portion of the inner cannula 30 (e.g., in portions distal of the compressible end region 32). Similarly, a 10 mm inner cannula 30 may have an inner diameter of about 9 mm. Accordingly, tubes sized to 6.5 mm, 7.0 mm, 7.5 mm, 8.0 mm, 8.5 mm, 9.0 mm, or 10 mm may feature smaller inner diameters that define the airflow passage.

Further, the inner diameter 62 at the proximal end 44 of the outer cannula 12 is typically larger than the inner diameter 60 and is selected to couple to appropriate tubing. That is, the outer cannula 12 is narrower in the inserted portion and is wider at the connector. The compressible end region 32 also has a larger outer diameter 70 relative to the inserted portion 54. In certain embodiments, the compressible end region may flare or taper outwards gradually such that the diameter increases gradually, with the largest diameter 70 at the proximal end 34. In other embodiment, the compressible end region 32 may include a generally barrel-shaped region with an outer diameter 70. It should be understood that the compressible end region 32 may change under compression. Accordingly, the outer diameter 70 refers to the uncompressed configuration. Further, in embodiments in which the proximal end 34 forms a broken annulus (i.e., is not a continuous element), the outer diameter 70 refers to a diameter between the solid portions of the proximal end 34. When the compressible end region 32 is within the outer cannula connector 28, the outer cannula connector 28 provides a biasing force that compresses the compressible end region 32 into a compressed configuration that is sized to fit within the inner diameter 62 of the outer cannula connector 28. The outer diameter 70 is larger than a largest outer diameter of the inner cannula 30 in the compressed configuration.

Figure 4:
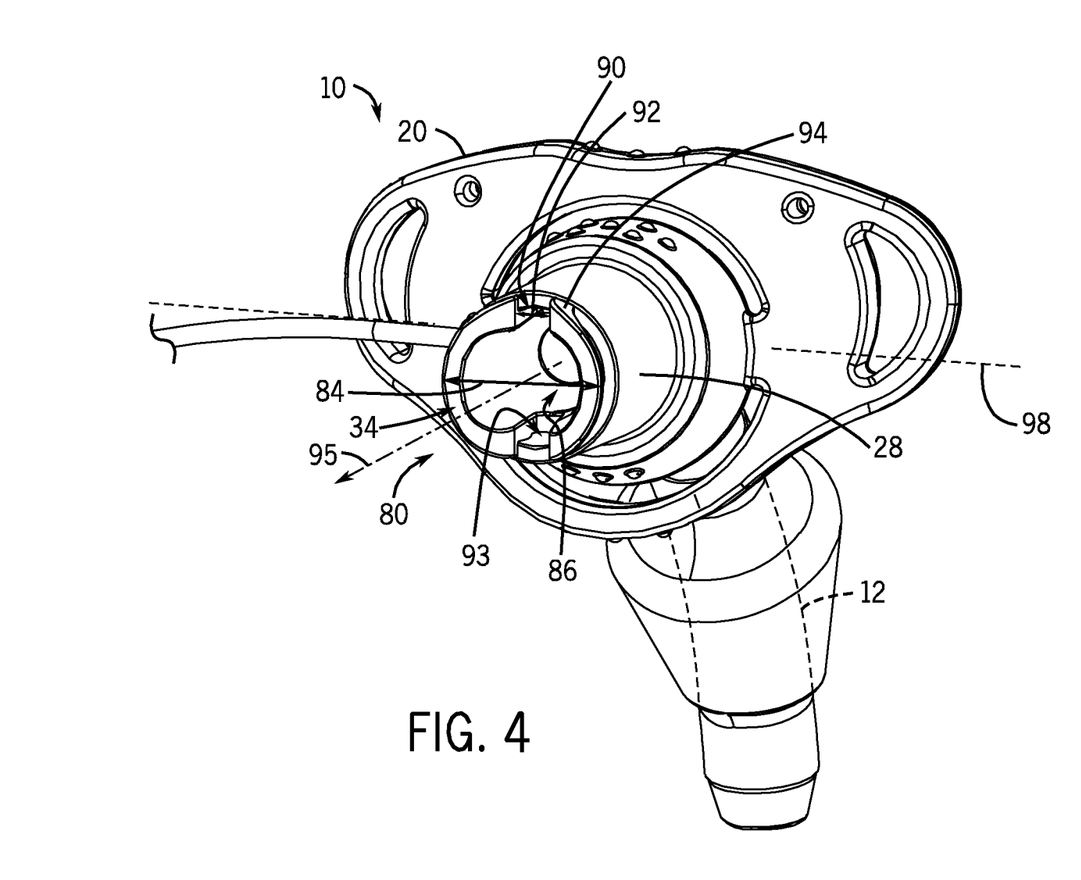
FIG. 4 is a partial perspective view of a tracheal tube with the inner cannula inserted in the outer cannula connector.

The compressed configuration of the inner cannula 30 is shown in FIG. 4, which is a partial perspective view of the proximal region 80 of the tracheal tube assembly 10. In the compressed configuration, the compressible end region 32 is constrained by the wall 82 of the outer cannula connector 28. Accordingly, the outer diameter 84 is smaller than the outer diameter 70 (see FIG. 3) of the uncompressed configuration. In one embodiment, the outer diameter 84 is about 15 mm or slightly smaller. That is, uncompressed outer diameter 70 is about the outer diameter of a 15 mm connector. The resulting proximal opening 86 of the inner cannula 30 is also smaller. In a specific embodiment, the material of the compressible end region 32 is selected so that an operator is capable of changing the configuration of the compressible end region 32 through the application of a biasing force. Similarly, the wall 82 of the outer cannula connector 28 is sufficiently strong to maintain the compressible end region 32 in the compressed configuration. In another embodiment, the compressible end region 32 includes one or more notches or openings 90 that facilitate the change from the uncompressed configuration to the compressed configuration. In the compressed configuration, the gap 92 formed by the opening 90 is smaller than in the uncompressed configuration.

The opening 90 allows the proximal end 34 of the inner cannula 30 to form a smaller compressed diameter 84 under a compression force without wrinkling and while maintaining a generally circular cross-section over the inserted portion of the compressible end region 32 that corresponds with the generally circular cross-section of the outer cannula connector 28. The size and number of openings 90 may be selected according to the size and manufacturing of the inner cannula 30. In one embodiment, the compressible end region has two openings 90. In embodiments with only one opening 90, the size of the gap 92 in the uncompressed configuration may be relatively larger to facilitate the change from uncompressed to compressed with fewer openings. In another embodiment, if more openings 90 are used, the corresponding gaps 92 may be smaller. That is, in certain embodiments, the total space accounted for in the gaps 92 is about the same regardless of the number of openings. The size of the gaps 92 may be measured in either the compressed or the uncompressed configuration, and may be a largest space between the adjacent portions of the inner cannula wall 94.

The outer cannula connector 28 may be formed in accordance with industry standards to permit and facilitate connection to ventilating equipment (not shown). By way of example, the outer cannula connector 28 is a 15 mm connector, although other sizes and connector styles may be used. Additionally, the tracheal tube assembly 10 may be connected to other medical devices, such as a suction device, a T-junction, a medicine delivery system, and so forth. Indeed, the outer cannula connector 28 may enable the attachment of one or more medical devices to the tracheal tube assembly 10. To accommodate such a connection, the compressible end region 32 may be formed such that, when inserted, the inner cannula 30 does not interfere with coupling via the outer cannula connector 28. To that end, in particular embodiments, the widest diameter 84 of the inner cannula 30, including any protruding portions, is smaller than the widest outer diameter (e.g., 15 mm) of the outer cannula connector 28. It should be understood that, the inserted portions of the compressible end region 32 press against the interior wall 93 of the outer cannula connector 28 and feature an outer diameter that is slightly smaller (e.g., 12 mm or smaller) than the inner diameter of the outer cannula connector 28. Further, the inner cannula 30 may feature regions with different outer diameters along its length in either configuration.

Because the inner cannula 30 is configured to be inserted and/or removed by an operator, the proximal end 34 may protrude from the outer cannula connector 28 to allow the compressible end region 32 to be manipulated while the inner cannula 30 is in place. For example, the proximal end 34 protrudes proximally or along a rotational axis 95 of the outer cannula connector 28. The axis 95 is generally orthogonal to the axis 98 along a longest dimension of the flange member 20. When inserted in the patient, the inner cannula 30 may be positioned so that the operator grips the proximal end and pushes laterally (e.g., along the axis 98). Accordingly, the openings 90 may be positioned to correspond with a dorsal and ventral side of the tube 10 (e.g. to correspond with the inner curve 50 and the outer curve 52 of the inner cannula, see FIG. 3) when inserted to encourage lateral compression. In other embodiment, the openings 90 may be positioned to encourage dorsal-ventral compression.

Figure 5:
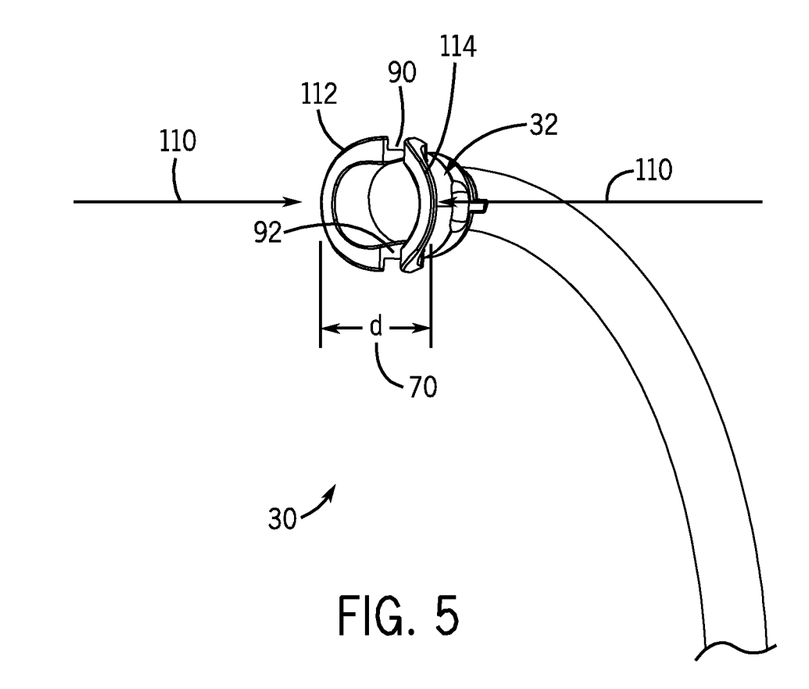
FIG. 5 is perspective view of an inner cannula with a compressible connector in accordance with embodiments of the present disclosure.

FIG. 5 is a perspective view of an inner cannula 30 in the uncompressed configuration. In the depicted configuration, the proximal end 34 assumes its largest unbiased outer diameter 70. When force is applied along arrows 110, the first ear 112 and the second ear 114 move towards one another (e.g., along axis 98, see FIG. 4) and the gaps 92 formed by the openings 90 decrease as the compressible end region 32 assumes the smaller, compressed outer diameter 84 (see FIG. 4). For example, an application of 5 N of force or less may be applied to achieve sufficient compression to insert the inner cannula 30. In other embodiments, the compressible end region 32 may form a single gripping structure or more than two ears.

Figure 6:
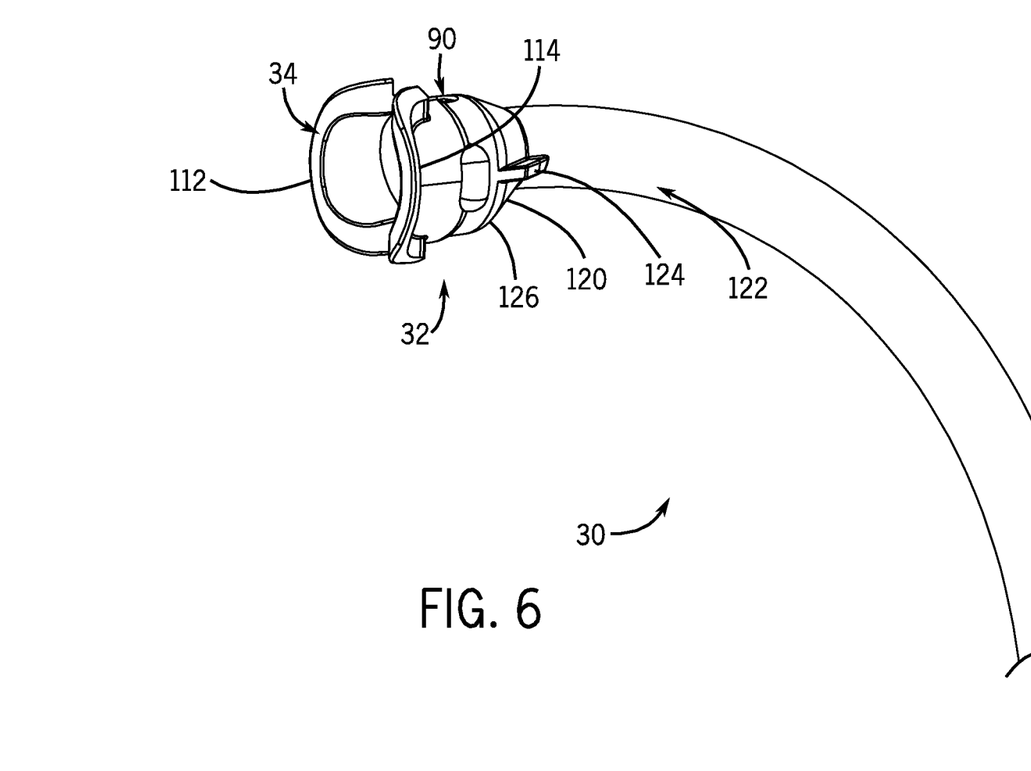
FIG. 6 is a partial perspective view of the compressible connector region of the inner cannula of FIG. 5.

FIG. 6 is a detail view of the compressible end region 32. In particular embodiments, the compressible end region 32 may include mating features that couple to complementary features on the interior wall 93 of the outer cannula connector 28 (see FIG. 4). Such mating features may prevent rotational movement of the inner cannula 30 relative to the outer cannula connector 28. In addition, the mating features may provide additional alignment to facilitate correct alignment of the curve of the inner cannula 30 with the curve of the outer cannula 12 (see FIG. 3). As depicted, the mating features may be protrusions, such as protrusion 122 formed on an exterior surface 120 of the inner cannula 30. The protrusion 122 may be formed in any suitable shape or combination of shapes, such as a rounded bump, a ramp shape, a pyramid structure, etc. Further, the compressible end region 32 may include any number of protrusions 122 positioned about a circumference. For example, the compressible end region 32 may include two protrusions 122 that oppose one another. In specific embodiments, opposing protrusions 122 may be circumferentially centered on the ears 112 and 114. In such embodiments, the protrusions 122 may serve as guides for an operator to press against to bias the ears 112 and 114 towards one another. In another embodiment, the protrusions 122 may be about 90 degrees from opposing notches 90. In another embodiment, respective protrusions 122 may be provided as a partial ring with an arc having less than 45° of circumference of the compressible end region 32. In another embodiment, the protrusion 122 may form a ring about the circumference of the compressible end region 32.

It should be understood that the mating features may also be implemented as recesses or a combination of protrusions and recesses. The size of the protrusion 122 may be selected to fit into a corresponding recess in the outer cannula connector 28 and may be less than a thickness of the wall of the outer cannula connector 28. In one embodiment, the protrusion 122 may protrude less than about 1 mm, less than about 1.5 mm or less than about 2 mm from the exterior surface 120. In particular embodiments, the protrusions 122 protrude less than a widest diameter 70 in an uncompressed configuration. Alternatively, the protrusion 122 may fit into complementary windows formed in the outer cannula connector. In such embodiments, the protrusion 122 may be larger. The inner cannula 30 may also include additional support structures, such as one or more ribs 124. In the depicted embodiment, the rib 124 may provide structural support to the protrusion 122. In addition, the compressible end region 32 may feature regions of varying outer diameters that form a slope 126. The slope 126 may be formed proximate to the protrusion 122 to facilitate insertion of the relatively larger protrusion 122 into the outer cannula connector 28.

Figure 7:
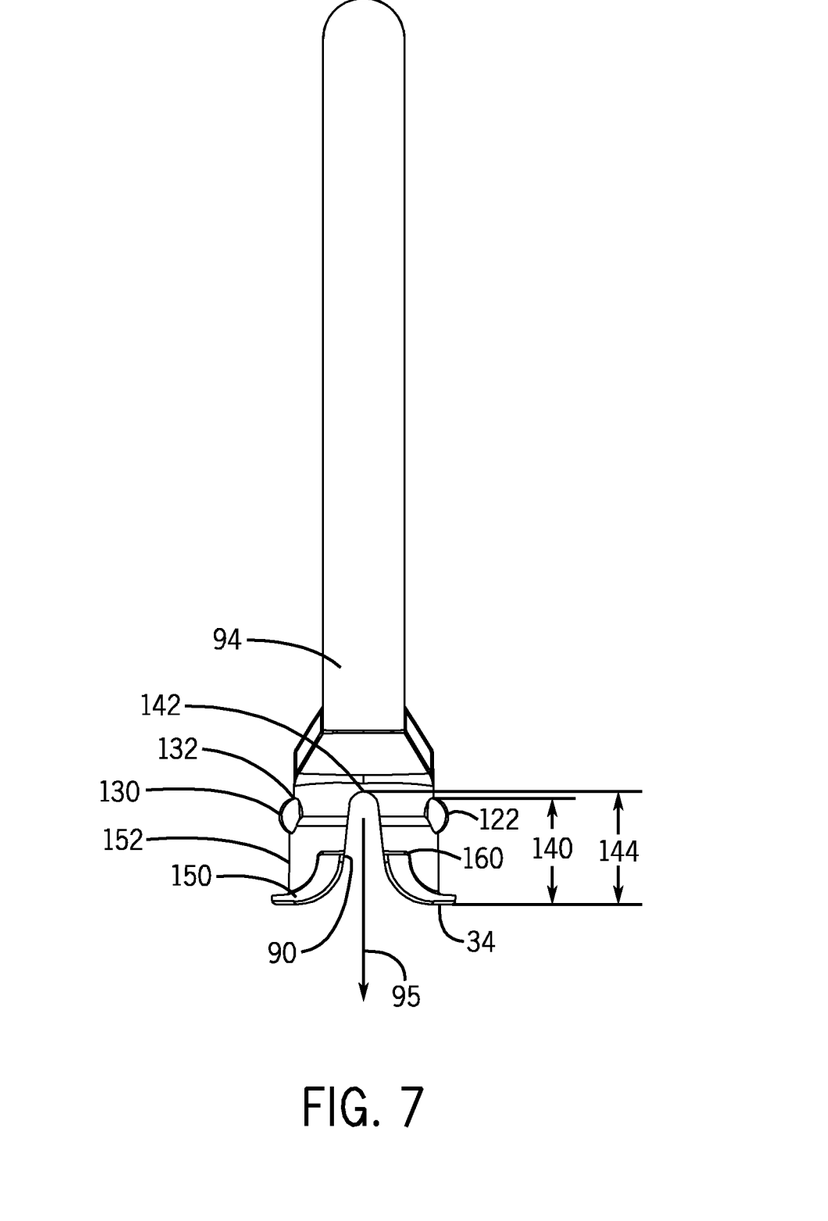
FIG. 7 is a top view of the compressible connector region of the inner cannula of FIG. 5

FIG. 7 is a top view of the inner cannula 30 showing the position of two opposing protrusions 122 relative to the proximal end 34. The position of the protrusions 122 may be measured from the midpoint 130 or the distal-most point 132. In one embodiment, the distance 140 from the proximal end 34 of the inner cannula 30 to the distal-most point 132 of the protrusion 122 may be selected to place the protrusion 122 within the interior of the outer cannula connector 28 (see FIG. 4). In another embodiment, the protrusion 122 may be positioned relative to a distal terminus 142 of opposing openings 90. As depicted, the openings 90 are generally oriented along the rotational axis 95. However, it should be understood that the openings 90 may be irregularly shaped. Accordingly, the distal terminus may be the distal-moist point of the opening 90 from the proximal end 34.

In one embodiment, the protrusion 122 is located proximally relative to the distal terminus 142. In other words, the distance 140 is less than a distance 144 (the distance from the proximal end 34 to the distal terminus 142). Further, the ratio of the distance 140 to the distance 144 may be selected such that the protrusions 122 are generally closer to the distal terminus 142 than the proximal end 34. For example, the ratio may be greater than 0.5 or greater than 0.75. Such an implementation may allow the protrusions 122 to be biased sufficiently toward one another to ease insertion in the outer cannula connector 28. That is, if the proximal end region 32 is flared, positions closer to the distal terminus 142 may be within smaller diameter regions. In certain embodiments, the distal terminus 142 is also positioned within the outer cannula connector 28. Depending on the size and length of the outer cannula connector 28, in particular embodiments, the distance 144 may be less than about 15 mm, less than about 12 mm, less than about 10 mm, less than about 9 mm, less than about 8 mm, less than about 7 mm, less than about 6 mm, or less than about 5 mm.

The proximal end 34 may also terminate in a lip 150 that is formed in the wall 94. The relatively thicker lip 150 may also extend at least partially towards the distal terminus 142 and terminate in an abutment surface 152. The abutment surface 152 is configured to abut the proximal end 44 of the inner cannula connector and prevent further movement of the inner cannula 30 distally, which may assist in aligning the inner cannula 30 within the outer cannula 12. In certain embodiments, a distance 160 from the abutment surface 152 to the proximal end 34 is less than the distance 140 and the distance 144. In particular embodiments, the distance 160 is less than 50% of the distance 144 or is less than 50% of the distance 140. In a particular embodiment, the distance 160 is about 4 mm. Further, in another embodiment, the distance between a midpoint 130 and the abutment surface 152 may be less than the distance 160, e.g., may be about 3 mm.

Figure 8:
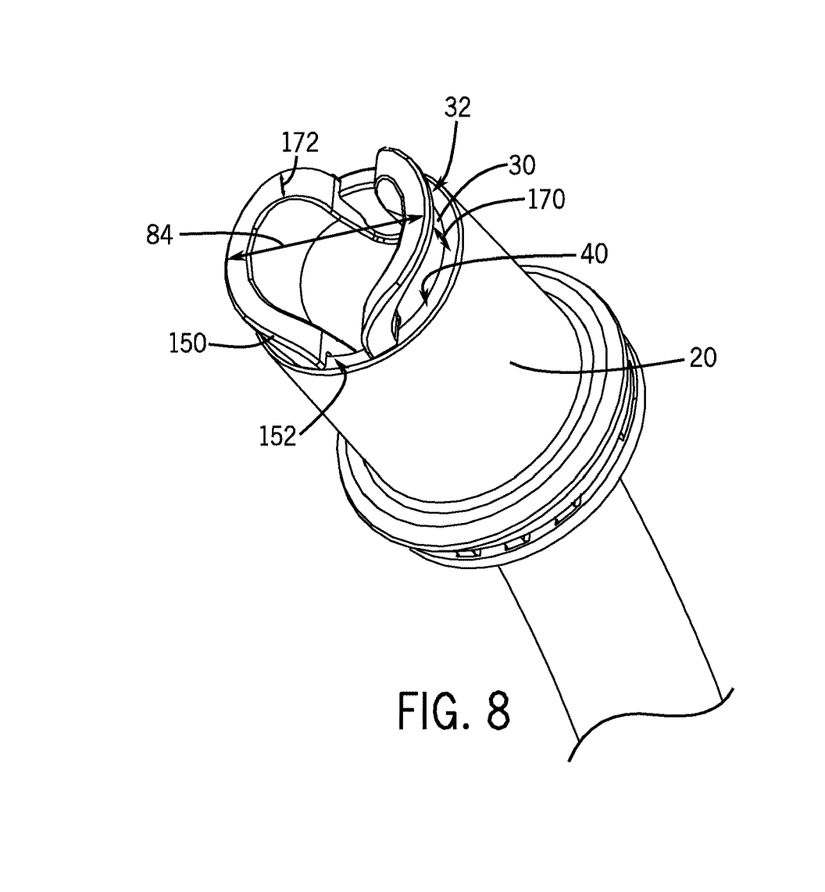
FIG. 8 is a partial perspective view of an inner cannula inserted into the outer cannula connector component.

As noted, the proximal end 34 of the inner cannula 30 is positioned outside of the outer cannula connector 28, which facilitates operator manipulation of the inner cannula 30. FIG. 8 is a partial perspective component view of the interaction between the outer cannula connector 28 and the proximal end 34. The position of the abutment surface 152 determines how much the proximal end 34 protrudes from the proximal end 44 of the outer cannula connector 28. A more distal abutment surface 152 results in greater protrusion. The length 170 of the protrusion may be about 4 mm or less. In other embodiments, the length 170 of the protrusion is selected to avoid interference with couplings formed by the outer cannula connector 28. In addition, the inner cannula 30 may include features that facilitate gripping by an operator. The thickness 172 of the lip 150 may be selected to maintain the desired outer diameter 84 and also form a gripping end. The lip 150 may be slightly thicker than the inserted portion of the compressible end region 32.

In certain embodiments of the present techniques, the inner cannula 30 is retained in place by the compression force of the compressible proximal end 32 against the interior surface 93 of the outer cannula connector 28. That is, the force against the outer cannula connector 28 reflects the material and geometric properties of the compressible end region 32 and a tendency of the compressible end region 32 to return to a default uncompressed configuration. In one embodiment, the compression force is sufficient to form a seal between the compressible end region 32 and the outer cannula connector 28. In one embodiment, the compressible end region 32 has one or more mating features that may align the inner cannula 30 within the outer cannula 12 and/or may prevent rotational dislodgment.

Figure 9:
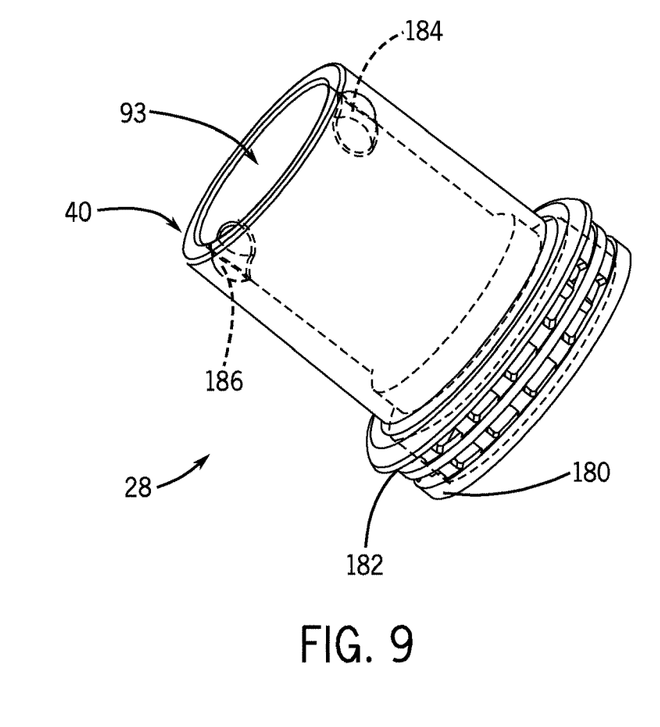
FIG. 9 is a perspective view of an outer cannula connector component.
Figure 10:
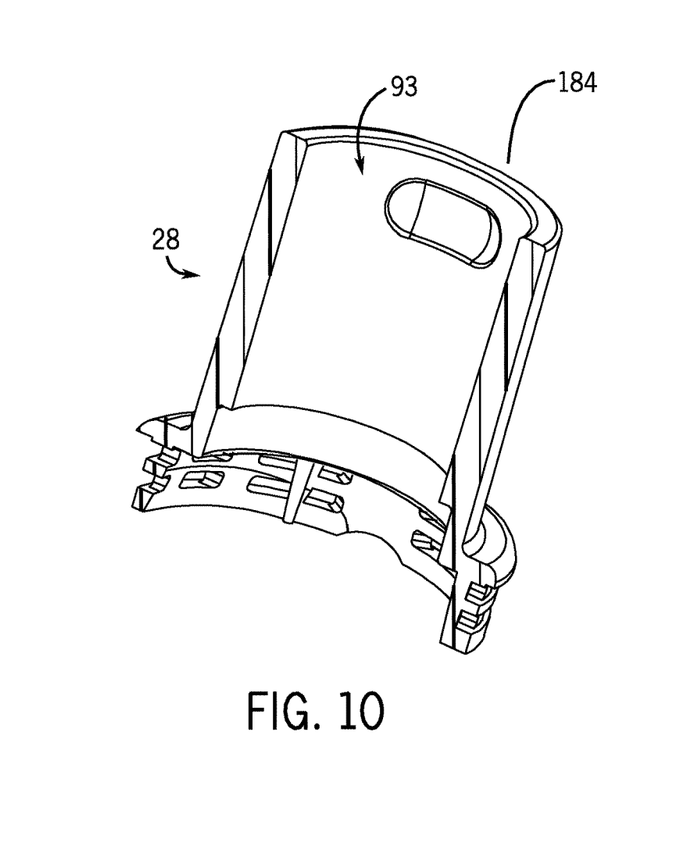
FIG. 10 is a cross-sectional view of the outer cannula connector component of FIG. 9.

FIG. 9 is a perspective view of an outer cannula connector 28 that includes complementary features to such mating features. The outer cannula connector 28 is typically coupled to the outer cannula 12 (see FIG. 1) at its distal end 180. The outer cannula connector 28 may also include distal features 182 for coupling to the flange member 20 (see FIG. 1), such as threading connectors, snap-in features, and/or one or more windows or recesses to facilitate heat bonding. In certain embodiments, the outer cannula connector 28 may include one or more recesses (e.g., recesses 184 and 186) that are sized and shaped to accommodate complementary protrusions on a compressible end region 32 of an inner cannula 30. It should be understood that the complementary features may be selected based on the characteristics of the mating features. Accordingly, if the mating features are protrusions, the complementary features are recess or windows and vice versa. Similarly, the position of the complementary features may be selected to facilitate proper alignment and insertion of the inner cannula 30. FIG. 10 is a cross-section of the outer cannula connector 28 of FIG. 9, showing the position of the recess 184.

Figure 11:
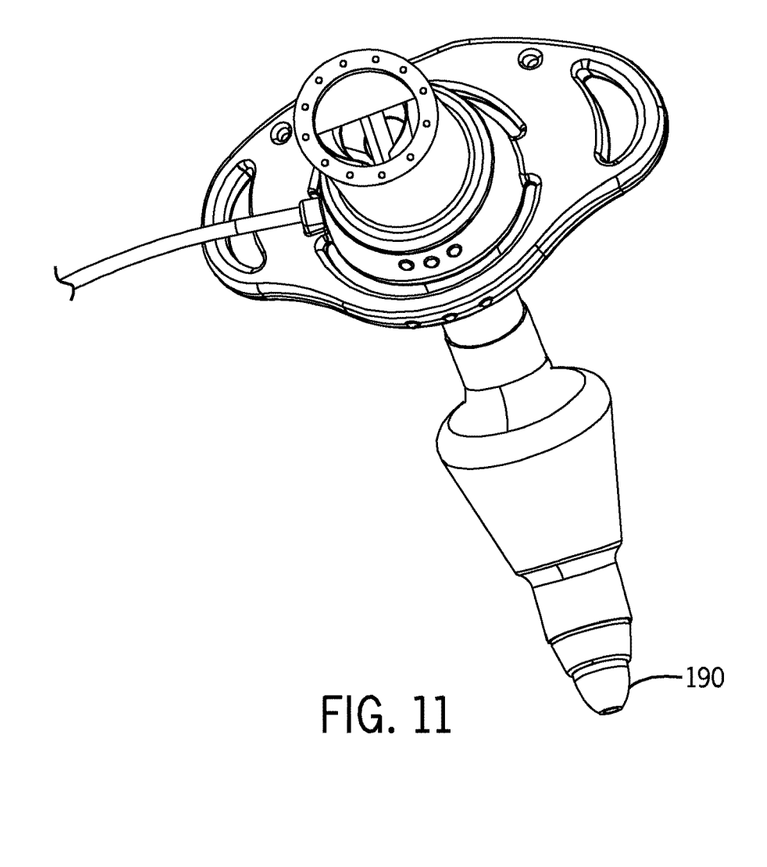
FIG. 11 is a perspective view of a tracheal tube assembly including an inner cannula with a compressible connector used in conjunction with an obturator.

It is envisioned that the tracheal tube assembly 10 as provided herein may be provided as an assembly and/or as a kit. A kit may include a packaging that encloses an inner cannula 30 sized for an outer cannula 12, which may include an affixed outer cannula connector 28 and flange member 20. The kit may also include a neck strap for retaining the tracheal tube 10 in place. The kit may also include an obturator 190, shown in FIG. 11. Other components of the kit may include a cap configured to be placed on a proximal end 34 while the obturator 190 is in use and that may be part of the obturator 190. The tube assembly 10 components (e.g., outer cannula 12, flange member 20, outer cannula connector 28, cuff 16, and pilot balloon assembly 18) may be assembled prior to in situ assembly of the inner cannula 30 into the outer cannula 12. Indeed, the user or clinician may perform final assembly of the tracheal tube 10 by selecting a desired inner cannula 30 from a selection of inner cannulas and then inserting the inner cannula 30 into the outer cannula 12 prior to intubation. Thus assembled, the tracheal tube 10 may then be inserted into the patient's trachea.

Components of the tube assembly 10 may be manufactured according to suitable techniques. For example, the inner cannula and/or outer cannula 12, including the outer cannula connector 28, may be molded, overmolded, two shot molded, computer numerical control (CNC) machined, milled, or otherwise formed into the desired shape. In one embodiment, a mold or mold form may be used to manufacture the inner cannula 30. In one embodiment, the mold or other manufacturing technique may facilitate a speckled outer surface of the inner cannula 30, which may facilitate insertion. One or more components may be manufactured of materials such as a polyethylene (e.g., low density polyethylene), polypropylene, PTFE, expandable PTFE, polyvinyl chloride (PVC), a PEBAX silicone, a polyurethane, thermoplastic elastomers, a polycarbonate plastic, a silicon, or an acrylonitrile butadiene styrene (ABS). In particular embodiments, the material of the inner cannula 30 may be selected to be 60 Shore D.

While the disclosure may be susceptible to various modifications and alternative forms, specific embodiments have been shown by way of example in the drawings and have been described in detail herein. However, it should be understood that the embodiments provided herein are not intended to be limited to the particular forms disclosed. Indeed, the disclosed embodiments may not only be applied to airway devices, but these techniques may also be utilized for connections between inner and outer conduits for other types of medical devices and medical connective tubing. Rather, the various embodiments may cover all modifications, equivalents, and alternatives falling within the spirit and scope of the disclosure as defined by the following appended claims.

What is claimed is:

1. A method comprising:
   compressing a proximal end of an inner cannula to assume a compressed configuration, wherein the proximal end comprises a first ear and a second ear separated by opposing notches formed in a wall of the proximal end, wherein the opposing notches extend from the proximal end towards a distal end of the inner cannula, wherein each notch of the opposing notches is adjacent to both the first and second ears such that the first and second ears are joined at a distal terminus of each notch of the opposing respective notches, and wherein the first ear and the second ear are configured to be biased towards one another in the compressed configuration; and
   inserting the inner cannula into an outer cannula via an outer cannula connector coupled to a proximal end of the outer cannula, wherein the outer cannula is configured to be positioned in a patient airway.

2. The method of claim 1, comprising removing the inner cannula from the outer cannula after a period of time.

3. The method of claim 2, comprising inserting a second inner cannula into the outer cannula via the outer cannula connector.

4. The method of claim 3, wherein the second inner cannula comprises a respective proximal end comprising a respective first ear and a respective second ear separated by opposing notches formed in a wall of the respective proximal end.

5. The method of claim 2, comprising cleaning a passageway of the outer cannula after the removing.

6. The method of claim 2, comprising disposing of the inner cannula after the removing.

7. The method of claim 1, wherein the proximal end of the inner cannula comprises a lip configured to be outside of the outer cannula connector when the inner cannula is inserted.

8. The method of claim 7, wherein the inserting comprises inserting the inner cannula until the lip abuts a proximal surface of the outer cannula connector.

9. The method of claim 1, wherein the proximal end comprises one or more mating features and wherein the inserting comprises aligning the one or more mating features with one or more complementary features of the outer cannula connector.

10. The method of claim 9, wherein the one or more mating features comprise a protrusion disposed on the first ear and wherein the one or more complementary features comprise a recess disposed on an interior wall of the outer cannula connector.

11. A method comprising:
    applying a compression force to a proximal end of an inner cannula, wherein the proximal end comprises a first ear, a second ear and at least one notch disposed at a terminus of the proximal end, and wherein the first ear and the second ear are joined together at a distal terminus of the at least one notch and move towards one another under the compression force; and
    inserting the inner cannula into an outer cannula during the applying, wherein the outer cannula is configured to be positioned in a patient airway.

12. The method of claim 11, wherein the proximal end comprises two notches, and wherein the two notches extend from the proximal end of the inner cannula towards a distal end of the inner cannula.

13. The method of claim 12, wherein the two notches are positioned opposite one another about a circumference of the proximal end.

14. The method of claim 12, wherein the two notches are aligned along an axis orthogonal to a longest dimension of a flange member coupled to the outer cannula connector.

15. The method of claim 11, comprising aligning one or more mating features disposed on the proximal region with complementary features on the outer cannula connector.

16. A method comprising:
    coupling an inner cannula to an outer cannula via a proximal end of the inner cannula, wherein the inner cannula is in a compressed configuration when coupled, wherein the proximal end comprises a first ear and a second ear separated by opposing notches formed in a wall of the proximal end, wherein the opposing notches extend from the proximal end towards a distal end of the inner cannula, wherein the first and second ears are joined together at a distal terminus of each notch of the respective opposing notches, and wherein the first ear and the second ear are configured to be biased towards one another in the compressed configuration.

17. The method of claim 16, comprising uncoupling the inner cannula from the outer cannula after a period of time.

18. The method of claim 16, comprising coupling connective tubing to the outer cannula connector, wherein the connective tubing is coupled to a ventilator.

19. The method of claim 18, comprising providing a user input to initiate patient ventilation from the ventilator through the inner cannula via the connective tubing.

20. The method of claim 16, wherein each notch of the opposing notches is adjacent to both the first and second ears.

* * * * *